United States Patent
Minakawa et al.

(10) Patent No.: US 8,524,452 B2
(45) Date of Patent: Sep. 3, 2013

(54) MEASUREMENT VALUE LOWERING INHIBITOR FOR IMMUNOASSAY METHOD AND IMMUNOASSAY METHOD USING THE SAME

(75) Inventors: Yasunori Minakawa, Gosen (JP); Michie Saito, Gosen (JP); Hiroshi Matsui, Gosen (JP)

(73) Assignee: Denka Seiken Co., Ltd., Tokyo (JP)

( * ) Notice: Subject to any disclaimer, the term of this patent is extended or adjusted under 35 U.S.C. 154(b) by 1719 days.

(21) Appl. No.: 10/590,785

(22) PCT Filed: Feb. 25, 2005

(86) PCT No.: PCT/JP2005/003135
§ 371 (c)(1),
(2), (4) Date: Aug. 25, 2006

(87) PCT Pub. No.: WO2005/086594
PCT Pub. Date: Sep. 22, 2005

(65) Prior Publication Data
US 2010/0143933 A1    Jun. 10, 2010

(30) Foreign Application Priority Data

Feb. 26, 2004 (JP) ................................. 2004-051184

(51) Int. Cl.
*G01N 33/53* (2006.01)
*G01N 33/531* (2006.01)
*G01N 33/536* (2006.01)

(52) U.S. Cl.
USPC ............. 435/7.1; 436/518; 436/534; 436/536

(58) Field of Classification Search
None
See application file for complete search history.

(56) References Cited

U.S. PATENT DOCUMENTS

| 4,454,232 A | 6/1984 | Breglio et al. |
| 5,972,718 A * | 10/1999 | Moghaddam et al. ........ 436/506 |

FOREIGN PATENT DOCUMENTS

| JP | 9-304384 A | 11/1997 |
| JP | 2002-340899 A | 11/2002 |
| JP | 2003-149244 A | 5/2003 |
| WO | WO 9002202 A1 * | 3/1990 |
| WO | WO 9110747 A1 * | 7/1991 |
| WO | WO-2004/092733 A1 | 10/2004 |

OTHER PUBLICATIONS

Fluke Catalog 1999/2000, pp. 1115, 1132.*

* cited by examiner

*Primary Examiner* — Shafiqul Haq
*Assistant Examiner* — Galina Yakovleva
(74) *Attorney, Agent, or Firm* — Birch, Stewart, Kolasch & Birch, LLP

(57) ABSTRACT

Disclosed is an agent for inhibiting decrease in measured values in immunoassays, which may reduce the influences by interfering substances in a test sample so as to promote the accuracy of the immunoassays, as well as an immunoassay and a reagent for immunoassays using the same, with which the decrease in the measured values due to the interfering substances is reduced. The agent for inhibiting decrease in measured values in immunoassays, caused by interfering substances, is an ionic surfactant having a molecular weight of 1000 to 100,000, the agent being a polymer in which a hydrophobic cyclic monomer(s) having an ionic functional group (s) is(are) polymerized.

10 Claims, No Drawings

MEASUREMENT VALUE LOWERING INHIBITOR FOR IMMUNOASSAY METHOD AND IMMUNOASSAY METHOD USING THE SAME

TECHNICAL FIELD

The present invention relates to an agent for inhibiting decrease in measured values in immunoassays, which decrease is caused by an interfering substance(s), as well as an immunoassay and reagent therefor using the same.

BACKGROUND ART

In clinical tests, there are a number of inspection items in which a biological sample is used as a test sample. Among them, in immunoassays, it is known that interfering substances exist, which influence on the immunological reactions of the target substances. The influence is one which influences on the accuracy of the measured values, and there are some reports thereon.

The most common method for confirming and reducing the influence by these interfering substances is the method in which the test sample is preliminarily diluted so as to decrease the concentrations of the interfering substances. However, with this method, since the concentration of the target substance is also decreased together with the concentrations of the interfering substances, it is difficult to employ this method when a substance having a low concentration in the sample is to be measured. Further, since the dilution operation is added, the time required for the measurement is prolonged, so that the quickness is reduced. On the other hand, if the interfering substance is known, a compound having a function to inhibit or suppress the interfering activity is added or a pretreatment such as warming is performed. However, these methods are effective only for known specific substances. It is thought that unknown substances may adversely affect the measurement depending on the measurement items.

Japanese Laid-open Patent Application (Kokai) No. 9-304384 discloses to use a conjugated diene polymer having sulfonic groups or salts thereof for avoiding false positive results. However, for promoting the accuracy of measurements, avoiding the interfering substances which may exist in all biological samples is needed rather than the substance causing false positive results contained in special samples.

Patent Literature 1: Japanese Laid-open Patent Application (Kokai) No. 9-304384

Problems which the Invention Tries to Solve

An object of the present invention is to provide an agent for inhibiting decrease in measured values in immunoassays, which may reduce the influence by interfering substances in test samples to promote the accuracy of immunoassays, as well as an immunoassay and reagent therefor using it, in which the decrease in the measured values by the interfering substances is inhibited.

Means for Solving the Problems

The present inventors intensively studied to discover that the influence by the interfering substances in test samples may be reduced so that the accuracy of the immunoassay may be promoted by making an ionic surfactant coexist in the reaction solution in which the immunoassay is carried out, the ionic surfactant being a polymer in which a hydrophobic cyclic monomer(s) having an ionic functional group(s) is(are) polymerized, thereby completing the present invention.

That is, the present invention provides an agent for inhibiting decrease in measured values in immunoassays, caused by an interfering substance(s), which agent is an ionic surfactant having a molecular weight of 1000 to 100,000, the ionic surfactant being a polymer in which a hydrophobic cyclic monomer(s) having an ionic functional group(s) is(are) polymerized. The present invention also provides an immunoassay which is carried out in the presence of the agent for inhibiting decrease in measured values in immunoassays according to the present invention. The present invention further provides a reagent for immunoassays, comprising at least a buffer and sensitized particles or an antiserum, characterized by further comprising the agent for inhibiting decrease in measured values in immunoassays according to the present invention. The present invention still further provides a use of the ionic surfactant as an agent for inhibiting decrease in measured values in immunoassays. The present invention still further provides a method for inhibiting decrease in measured values in immunoassays, which method comprises making the ionic surfactant coexist in the reaction solution of the immunoassay.

Effects of the Invention

By carrying out an immunoassay in the presence of the agent for inhibiting decrease in measured values in immunoassays, according to the present invention, the influence by the interfering substance(s) in the test sample is reduced, so that the accuracy of the immunoassay is promoted when compared with the case wherein the immunoassay is carried out in the absence of the agent for inhibiting decrease in measured values.

BEST MODE FOR CARRYING OUT THE INVENTION

Among the immunoassays, immunoagglutination method is a method for detecting or quantifying an antigen or antibody in a test sample based on the change in an optical property such as turbidity or absorbance of the reaction solution, which change is caused by antigen-antibody reaction. Immunoagglutination method includes turbidimetric immunoassay and immunonephelometry. To increase the sensitivity of the measurement, an antibody or antigen which undergoes antigen-antibody reaction with the target antigen or target antibody in the test sample is immobilized on particles (sensitized particles) such as latex particles, and the detection or quantification is carried out based on the change in an optical property caused by agglutination of the sensitized particles due to the antigen-antibody reaction. (the method in which latex particles are used is also specifically called latex agglutination method). However, antiserum is also often used without using the sensitized particles.

The agent for inhibiting decrease in measured values in immunoassays according to the present invention is an ionic surfactant having a molecular weight of 1000 to 100,000. The ionic surfactant is a polymer in which a hydrophobic cyclic monomer(s) having an ionic functional group(s) is(are) polymerized.

Preferred examples of the ionic functional group include sulfonic group and salts thereof, carboxylic group and salts thereof, and amines (quaternary amine or the like which is ionized in aqueous solution). Sulfonic group and salts thereof are especially preferred. Thus, the ionic surfactant may be either an anionic surfactant or cationic surfactant.

Examples of the hydrophobic ring include aromatic rings and cycloalkyl rings. The hydrophobic ring may be a heteroring containing an oxygen atom(s), nitrogen atom(s), sulfur atom(s) and/or the like, or may be a fused ring resulting from fusion of the heterorings. As the hydrophobic ring, aromatic rings are preferred. Examples of the aromatic rings include benzene ring, naphthalene ring and anthracene ring. Among these rings, benzene ring and naphthalene ring are preferred, and benzene ring is most preferred.

Examples of preferred polymers used as the agent for inhibiting decrease in measured values include sodium polyanethole sulfonate, sodium polystyrene sulfonate, sodium salt of condensate between naphthalene sulfonic acid and formalin, sodium salt of condensates between an aromatic sulfonic acid and formalin (more concretely, DISROL (trade name, produced by Nippon Nyukazai Co., Ltd.), DEMOL (trade name, produced by Kao Corporation), POLITY PS-1900 (Lion Corporation) and POLITY N-100K (trade name, produced by Lion Corporation).

Examples of the preferred polymers include those containing a recurring unit(s) represented by the following Formula [I]:

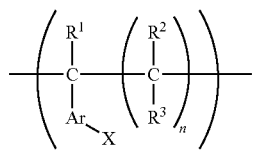

[I]

wherein Ar represents a hydrophobic ring; X represents the ionic functional group; $R^1$ to $R^3$ independently represent hydrogen or alkyl; n represents an integer of 0 to 10; hydrogen atom(s) bound to a carbon atom(s) constituting Ar optionally being substituted with a substituent(s) which does(do) not adversely affect the effect of the present invention.

In the above-described Formula [I], X and Ar represent the above-described ionic functional group and hydrophobic ring, respectively. In cases where $R^1$ to $R^3$ are alkyl groups, lower alkyl groups are preferred (In the present Description and in the Claims, the term "lower" means $C_1$-$C_4$). Further, n is preferably 0 to 3. The hydrogen atom(s) bound to a carbon atom(s) constituting Ar may optionally be substituted with a substituent(s) which does(do) not adversely affect the effect of the present invention. Examples of such a substituent include lower alkyl groups and lower alkoxyl groups.

Among the recurring units represented by the Formula [I], those represented by the following Formula [II] are preferred:

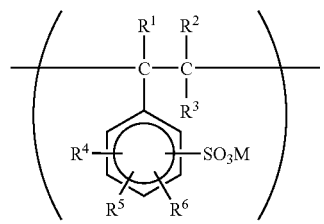

[II]

wherein M represents an atom or a group which becomes a monovalent cation in aqueous solution, preferably an alkaline metal such as sodium or potassium; $R^1$ to $R^3$ independently represent hydrogen or lower alkoxyl; and $R^4$ to $R^6$ independently represent hydrogen or lower alkyl.

Among the recurring units represented by the above-described Formula [I], especially preferred are the anethole sulfonic acid salts represented by the following Formula [III], styrene sulfonic acid salts represented by the following Formula [IV], and salts of condensate between naphthalene sulfonic acid and formalin represented by the following Formula [V].

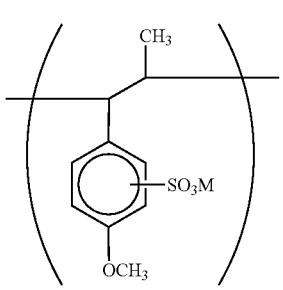

[III]

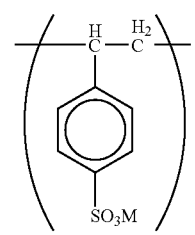

[IV]

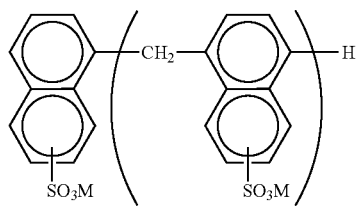

[V]

wherein in Formulae [III], [IV] and [V], M has the same meaning as in Formula [I], and is preferably an alkaline metal such as sodium or potassium.

The molecular weight of the polymer is 1000 to 100,000, and preferably 1000 to 60,000.

The above-described recurring units may be employed individually or two or more of them may be employed in combination. Although the polymer used as the agent for inhibiting decrease in measured values preferably consists of only the above-described recurring unit(s), the polymer may comprise other unit(s) to the extent that the effect of the present invention is not adversely affected. The content of such a unit(s) in the polymer is usually not more than 20 mol %, preferably not more than 10 mol %, still more preferably not more than 5 mol %.

The immunoassay according to the present invention is carried out in the presence of the above-described agent for inhibiting decrease in measured values according to the present invention. The amount of the agent for inhibiting decrease in measured values to be used is not restricted, and usually 0.01% to 5% (weight/volume), preferably about 0.1 to 1% in terms of the final concentration in the reaction solution. It is preferred, however, to select the concentration optimum for attaining the effect, depending on the type of the macromolecular ionic surfactant, the mixing ratio among the test sample, buffer and the antiserum or sensitized latex particles, and so on.

The test sample to be subjected to the immunoassay according to the present invention is not restricted, and biological samples with which the effect of the present invention, that is, to reduce the influence by the interfering substances is greatly exerted, are preferred. Preferred examples thereof include body fluids such as blood, serum, blood plasma, urine, feces, saliva, tissue fluids, spinal fluid and swabs, as well as dilutions thereof. Blood, serum and blood plasma, as well as dilutions thereof are especially preferred.

In cases where the immunoassay is an immunoagglutination method, the antibody or antigen sensitized on the sensitized particles is not restricted. Examples of them include, as in conventional methods, C-reactive protein (CRP), rheumatoid factor (RF), ferritin (FER) and myoglobin (Mb) as well as antibodies thereto, but the antigens and the antibodies are not restricted thereto.

The immunoassays according to the present invention may be carried out in the same manner as the conventional immunoassays except that the immunoassays are carried out in the presence of the above-described agent for inhibiting decrease in measured values. That is, in cases where the immunoassay is an immunoagglutination method, the concentration of the sensitized particles in the reaction solution is not restricted and is usually about 0.01 to 0.5%, and the reaction is usually carried out at 1° C. to 56° C., preferably at 37° C. for about 1 minute to 10 minutes. It should be noted, however, the reaction conditions are not restricted thereto. As the reaction medium, various buffers such as glycine buffer may usually be used. The turbidity or absorbance of the reaction solution is measured before the reaction and at a prescribed time after the reaction, or before the reaction and at time points thereafter, and the detection or quantification of the test substance is carried out based on the amount of the change in the turbidity or absorbance (end-point method) or on the rate of the change thereof (rate method). The immunoagglutination method may be carried out manually or by using an automatic analyzer.

In cases where the immunoassay is an agglutination method, in the method of the present invention, although the agent for inhibiting decrease in measured values and the sensitized particles or antiserum may be mixed simultaneously with the test sample, it is preferred that the method comprise a first step of bringing a test sample into contact with the agent for inhibiting decrease in measured values; and a second step of subjecting the test sample to antigen-antibody reaction with sensitized particles or with an antiserum, in order to maximally obtain the effect of the present invention. In this case, in both of the first and second steps, the reaction time is usually 1 minute to 10 minutes, preferably 1 minute to 5 minutes, and the reaction temperature is usually 1° C. to 56° C., preferably 37° C., although the reaction conditions are not restricted thereto. Further, in cases where the reaction is carried out in two steps, the concentration of the agent for inhibiting decrease in measured values in the reaction solution of the first step is preferably 0.01% to 5% (weight/volume), more preferably about 0.05 to 1%.

The immunoassay according to the present invention is not restricted to immunoagglutination method, but includes sandwich methods such as sandwich ELISA, immunochromatography, competition methods and so on. These immunoassays may also be carried out by conducting the respective immunoassay in the presence of the agent for inhibiting decrease in measured values according to the present invention in the medium of the immunological reaction. In these cases, the concentration of the agent for inhibiting decrease in measured values may be the same as described above.

The present invention also provides a reagent for immunoassays comprising a buffer, sensitized particles and the above-described agent for inhibiting decrease in measured values. In cases where the immunoagglutination method is carried out in two steps, in view of the ease of handling and of the stability of the reagent, the reagent may preferably be a binary liquid reagent comprising a first reagent including at least a buffer, the first reagent being firstly mixed with a test sample; and a second reagent including at least a buffer and the sensitized particles, the second reagent being added to the mixture of the test sample and the first reagent. In this case, the concentration of the agent for inhibiting decrease in measured values in the first reagent is usually, but not limited to, 0.01 to 5% (w/v), preferably about 0.01 to 1% (w/v).

The present invention will now be described concretely by way Examples thereof. It should be noted that the present invention is not restricted to the Examples below.

Example 1

Reagents

A reagent for latex turbidimetric assay for measuring myoglobin having the following composition was prepared:

| First Reagent |
| --- |
| 170 mM glycine buffer, pH 7.0 |
| 50 mM EDTA |
| 100 mM sodium chloride |
| 0.3% sodium polyanethole sulfonate (molecular weight 40,000) |

Second Reagent

Mb-Latex "SEIKEN"/Latex suspension (produced by Denka Seiken)

Example 2

Reagents

A reagent for latex turbidimetric assay for measuring myoglobin having the following composition was prepared:

| First Reagent |
| --- |
| 170 mM glycine buffer, pH 7.0 |
| 50 mM EDTA |
| 100 mM sodium chloride |
| 0.3% sodium polystyrene p-sulfonate (molecular weight 14,000) |

Second Reagent

Mb-Latex "SEIKEN"/Latex suspension (produced by Denka Seiken)

Comparative Example 1

For comparison, a reagent for latex turbidimetric assay for measuring myoglobin having the following composition was prepared, which did not contain the sodium polyanethole sulfonate or sodium polystyrene p-sulfonate:

| First Reagent |
| --- |
| 170 mM glycine buffer, pH 7.0 |
| 50 mM EDTA |
| 100 mM sodium chloride |

Second Reagent

Mb-Latex "SEIKEN"/Latex suspension (produced by Denka Seiken)

were compared according to the presence or absence of the agent for inhibiting decrease in measured values in the first reagent.

The results are shown in Table 1. In Table 1, the term "Theoretical Value" means the value measured at a dilution concentration of 1/10 (10-fold dilution) at which the decrease in the measured values caused by the coexisting interfering substances may be ignored, multiplied by the numerator of the dilution concentration (when the dilution concentration is 10/10, the value is multiplied by 10, and when the dilution concentration is 2/10, the value is multiplied by 2). The term "Difference (%)" means ((theoretical value)−(measured value))/(theoretical value)×100(%), and smaller difference (%) means smaller deviation from the theoretical value.

TABLE 1

| Dilution Concentration | Comparative Example 1 | | | Example 1 | | | Example 2 | | |
| --- | --- | --- | --- | --- | --- | --- | --- | --- | --- |
| | Measured Value | Theoretical Value | Difference (%) | Measured Value | Theoretical Value | Difference (%) | Measured Value | Theoretical Value | Difference (%) |
| 1/10 | 63 | 63 | 0% | 61 | 61 | 0% | 63 | 63 | 0% |
| 2/10 | 114 | 126 | 10% | 121 | 122 | 1% | 124 | 126 | 2% |
| 3/10 | 152 | 189 | 20% | 181 | 183 | 1% | 186 | 189 | 2% |
| 4/10 | 200 | 252 | 21% | 238 | 244 | 2% | 239 | 252 | 5% |
| 5/10 | 233 | 315 | 26% | 296 | 305 | 3% | 299 | 315 | 5% |
| 6/10 | 287 | 378 | 24% | 354 | 366 | 3% | 361 | 378 | 4% |
| 7/10 | 316 | 441 | 28% | 416 | 427 | 4% | 422 | 441 | 4% |
| 8/10 | 357 | 504 | 29% | 471 | 488 | 3% | 486 | 504 | 4% |
| 9/10 | 398 | 567 | 30% | 526 | 549 | 4% | 542 | 567 | 4% |
| 10/10 | 424 | 630 | 33% | 581 | 610 | 5% | 603 | 630 | 4% |

(Unit of measured values and theoretical values: ng/ml)

It should be noted that as the buffer used in the first and second reagents in Examples 1 and 2 and in Comparative Example 1, phosphate buffer, Good's buffer or the like may also be used, and a preferred pH of the buffer may be employed.

Measurement Examples

Test Sample Randomly Selected One Clinical Sample (Serum)

Measurement Method Preparation of Sample: The test sample is serially diluted in 1/10 (10-fold dilution) to 10/10 (not diluted) with physiological saline as a diluent.
Measurement Method Measurement by Toshiba TBA-30R Automatic Analyzer Measurements were performed using the respective reagents prepared in Examples 1 and 2 and in Comparative Example 1. To 20 μL of the sample prepared as described above, 2004 of the first reagent was added and the mixture was stirred at 37° C. After leaving the mixture to stand for 5 minutes, 100 μL of the second reagent was added and the resulting mixture was stirred at 37° C., followed by measuring the agglutination reaction in about 2 minutes in terms of the amount of the change in absorbance at 570 nm. Samples having known concentrations had been preliminarily subjected to the measurement under the same conditions, and a calibration curve showing the relationship between the concentration and the amount of the change in absorbance had been preliminarily prepared. The measured values (ng/mL)

As shown in Table 1, in Comparative Example 1 which did not contain the agent for inhibiting decrease in measured values, the difference between the measured value of the non-diluted sample (dilution concentration 10/10) and the theoretical value was as high as 33%, while in Examples 1 and 2 according to the present invention, the differences were 5% and 4%, respectively, even with the non-diluted samples. These results indicate that by addition of the agent for inhibiting decrease in measured values according to the present invention, the difference between the theoretical value and the measured value is made small. Thus, it was proved that the accuracy of the measured values is greatly promoted by the reduction of the influence by the interfering substances.

The invention claimed is:

1. An immunoagglutination immunoassay for detecting and quantifying a target substance in a test sample comprising in sequential order:

(a) bringing the test sample into contact with an agent, which agent inhibits a decrease in measured values, wherein said decrease is caused by an interfering substance(s) present in the test sample; and (b) subjecting the test sample to an antigen-antibody reaction with sensitized particles or with an anti-serum, wherein said agent is an ionic surfactant having a molecular weight of 1000 to 100,000, and said ionic surfactant being a polymer, wherein said polymer comprises a recurring unit represented by the following Formula [I]:

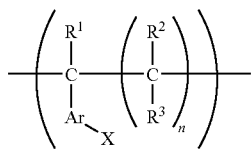

[I]

wherein Ar represents a hydrophobic ring; X represents the ionic functional group; $R^1$ to $R^3$ independently represent hydrogen or alkyl; n represents an integer of 0 to 10; hydrogen atom(s) bound to a carbon atom(s) constituting Ar optionally being substituted with a substituent(s) which does(do) not adversely affect the effect of the present invention, wherein the sensitized particles or the antiserum specifically react with the target substance, and wherein upon performing steps (a) and (b), the target substance is capable of being detected or quantified by measuring the agglutination resulting from the antigen-antibody reaction with sensitized particles or with the anti-serum.

2. The immunoassay according to claim 1, wherein said test sample is a biological sample.

3. The immunoassay according to claim 2, wherein said test sample is blood, serum or blood plasma.

4. The immunoassay according to claim 1, wherein the concentration of said agent for inhibiting the decrease in measured values in immunoassays in reaction solution is 0.01% to 5% (weight/volume).

5. The immunoassay according to claim 1, wherein said hydrophobic cyclic monomer is an aromatic monomer.

6. The immunoassay according to claim 5, wherein said aromatic monomer has a benzene ring.

7. The immunoassay according to claim 1, wherein said ionic functional group is sulfonic group or a salt thereof, carboxylic group or a salt thereof, or an amine.

8. The immunoassay according to claim 7, wherein said ionic functional group is sulfonic group or a salt thereof.

9. The immunoassay according to claim 1, wherein said recurring unit is represented by the following Formula [II]:

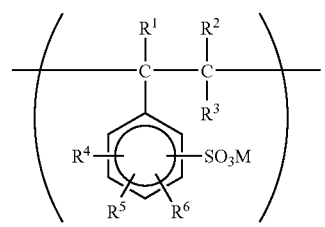

[II]

wherein M represents an atom or a group which becomes a monovalent cation in aqueous solution; $R^1$ to $R^3$ have the same meanings as said $R^1$ to $R^3$ in said Formula [I]; and $R^4$ to $R^6$ independently represent hydrogen, lower alkoxyl or lower alkyl.

10. The immunoassay according to claim 7, wherein said recurring unit is an anethole sulfonic acid salt or styrene sulfonic acid salt.

* * * * *